US008974506B2

(12) United States Patent
Wenger et al.

(10) Patent No.: US 8,974,506 B2
(45) Date of Patent: Mar. 10, 2015

(54) MEDICAL DEVICE, APPARATUS, AND SURGICAL METHOD

(75) Inventors: Andreas Wenger, Muri b. Bern (CH); Jörg Mayer, Niederlenz (CH)

(73) Assignee: SpineWelding AG, Schlieren (CH)

( * ) Notice: Subject to any disclaimer, the term of this patent is extended or adjusted under 35 U.S.C. 154(b) by 22 days.

(21) Appl. No.: 13/505,784

(22) PCT Filed: Nov. 9, 2010

(86) PCT No.: PCT/CH2010/000278
§ 371 (c)(1),
(2), (4) Date: May 17, 2012

(87) PCT Pub. No.: WO2011/054122
PCT Pub. Date: May 12, 2011

(65) Prior Publication Data
US 2012/0221062 A1 Aug. 30, 2012

Related U.S. Application Data

(60) Provisional application No. 61/259,383, filed on Nov. 9, 2009, provisional application No. 61/388,243, filed on Sep. 30, 2010, provisional application No. 61/394,580, filed on Oct. 19, 2010.

(51) Int. Cl.
A61B 17/58 (2006.01)
A61B 17/68 (2006.01)
(Continued)

(52) U.S. Cl.
CPC ............ *A61B 17/68* (2013.01); *A61B 17/8811* (2013.01); *A61B 17/8822* (2013.01); *A61C 8/0033* (2013.01); *A61B 17/320068* (2013.01);
(Continued)

(58) Field of Classification Search
USPC ............ 606/264–275, 300–321; 411/23, 82.1
See application file for complete search history.

(56) References Cited

U.S. PATENT DOCUMENTS 3,025,853 A 3/1962 Mason
5,492,442 A 2/1996 Lasner
(Continued)

FOREIGN PATENT DOCUMENTS

EP 0411273 2/1991
EP 2 269 526 B1 * 1/2009 ............. A61B 17/86
(Continued)

*Primary Examiner* — Todd Manahan
*Assistant Examiner* — Jessica Weiss
(74) *Attorney, Agent, or Firm* — Rankin, Hill & Clark LLP

(57) ABSTRACT

A medical device is provided, the device, for example, being implantable into a human or animal body or being an augmentation device for strengthening human or animal hard tissue for subsequent implantation of a separate implant. The device includes a sheath element suitable of being brought into contact, during a surgical operation, with live hard tissue and/or with hard tissue replacement material. The sheath element has a, for example, generally elongate shape and a longitudinal bore defining a longitudinal opening reaching from a proximal end of the sheath element into a distal direction, and a plurality of holes in a wall of the opening. Further, the device includes a liquefiable element that is insertable or inserted in the longitudinal opening and at least partly liquefiable by the impact of energy impinging from the proximal side.

14 Claims, 3 Drawing Sheets

(51) Int. Cl.
  *A61B 17/88*  (2006.01)
  *A61C 8/00*  (2006.01)
  *A61B 17/32*  (2006.01)
  *A61B 17/70*  (2006.01)
  *A61B 17/86*  (2006.01)
  *A61C 19/06*  (2006.01)

(52) U.S. Cl.
  CPC .......... *A61B 17/7098* (2013.01); *A61B 17/864* (2013.01); *A61B 17/866* (2013.01); *A61C 19/063* (2013.01)
  USPC ............ 606/304; 606/309; 411/23; 411/82.1

(56) References Cited

U.S. PATENT DOCUMENTS

| | | |
|---|---|---|
| 6,585,740 B2 | 7/2003 | Schlapfer et al. |
| 2007/0299450 A1 | 12/2007 | Her et al. |
| 2008/0262517 A1 | 10/2008 | Wieland |
| 2009/0018560 A1 | 1/2009 | Mayer et al. |
| 2009/0036986 A1 | 2/2009 | Lancial et al. |
| 2013/0184761 A1 | 7/2013 | Biedermann et al. |

FOREIGN PATENT DOCUMENTS

| | | | | |
|---|---|---|---|---|
| EP | 2014247 | 1/2009 | | |
| EP | 2572663 | 3/2013 | | |
| JP | 2005536255 | 12/2005 | | |
| JP | 2009536079 | 10/2009 | | |
| WO | 90/02526 | 3/1990 | | |
| WO | 02/069817 | 9/2002 | | |
| WO | 2009/010247 | 1/2009 | | |
| WO | WO2009/010247 | * 1/2009 | ............ | A61B 17/86 |
| WO | 2009/132472 | 11/2009 | | |
| WO | WO 2009/132472 | * 11/2009 | ............ | A61B 17/68 |

* cited by examiner

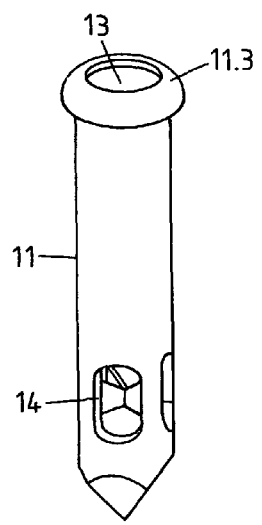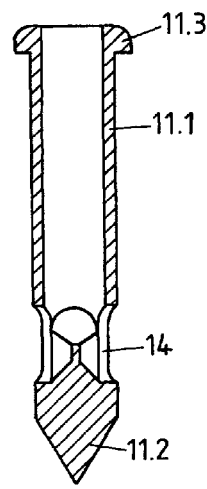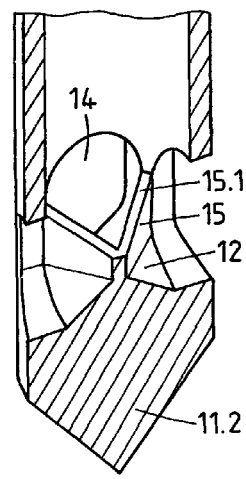
Fig. 3　　　Fig. 4　　　Fig. 5
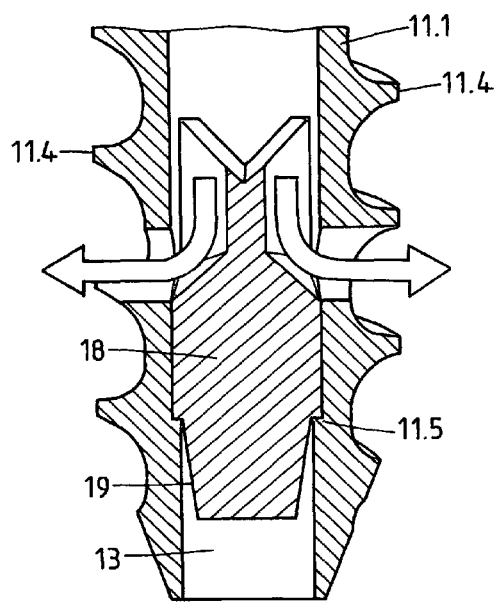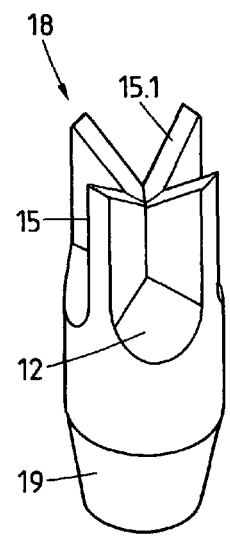
Fig. 6　　　Fig. 7

MEDICAL DEVICE, APPARATUS, AND SURGICAL METHOD

This application is the U.S. national phase of International Application No. PCT/CH2010/000278 filed Nov. 9, 2010 which designated the U.S. and claims the benefit of and priority to U.S. Provisional Application Ser. No. 61/259,383, filed Nov. 9, 2009, and U.S. Provisional Application Ser. No. 61/388,243, filed Sep. 30, 2009, and U.S. Provisional Application Ser. No. 61/394,580, filed Oct. 19, 2010, the entire contents of each of which are hereby incorporated by reference.

BACKGROUND OF THE INVENTION

1. Field of the Invention

The invention is in the field of medical technology. In particular, it relates to medical devices, medical apparatus and medical methods, especially to implants, apparatuses for implantation, and implantation methods.

2. Description of Related Art

If screws are anchored in live bone tissue, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or osteopenic or otherwise weakened bone tissue.

One solution of this problem is the use of an alternative anchoring method that is suitable also for tissue in which screws are not stable. The publications WO 02/069817, WO 2004/017 857, WO 2008/034 277, and WO 2009/055 952 concern anchorage of an implant in bone tissue with the aid of mechanical vibration and a thermoplastic material which is liquefiable by the mechanical vibration, i.e. the thermoplastic material is capable of being liquefied when vibrated and simultaneously kept in contact with a non-vibrating surface. The thermoplastic material, where in contact with the bone tissue, is liquefied and pressed into pores or cavities of the bone tissue to constitute, when re-solidified, a positive fit connection with the bone tissue.

A special group of embodiments of implants and implant anchoring processes is based on the liquefiable material being inserted (pre-assembled or inserted in situ) in a longitudinal bore of a sheath element. The sheath element comprises at least one hole in the sheath element wall, through which the liquefied material is pressed from the longitudinal bore into the structures (pores or cavities or other structures) of the bone tissue or other hard tissue or hard tissue replacement material in which anchoring is desired. This principle of pressing liquefied material out of a tube or sleeve element with lateral openings is for example described in U.S. Pat. No. 7,335,205, U.S. Pat. No. 6,921,264, WO 2009/055 952, WO 2009/010247, WO 2009/010234, and PCT application No. PCT/CH 2009/000138, all of which are incorporated herein by reference.

BRIEF SUMMARY OF THE INVENTION

It is an object of the present invention to provide a medical device being an implant or an augmentation device overcoming drawbacks of prior art implants or augmentation devices. It is a further object of the invention to provide an improved implant that comprises a sheath element and a plurality of holes through which liquefied liquefiable material is pressed into adjacent hard tissue and/or hard tissue replacement material.

In accordance with an aspect of the invention, a medical device is provided, the device, for example, being implantable into a human or animal body or being an augmentation device for strengthening human or animal hard tissue for subsequent implantation of a separate implant, the device comprising a sheath element suitable of being brought into contact, during a surgical operation, with live hard tissue and/or with hard tissue replacement material. The sheath element has a for example generally elongate shape and a longitudinal bore defining a longitudinal opening reaching from a proximal end of the sheath element into a distal direction, and a plurality of holes in a wall of the opening. At least two of the holes may have an approximately equal axial position. Further, the device comprises a liquefiable element that is insertable or inserted in the longitudinal opening and at least partly liquefiable by the impact of energy impinging from the proximal side so that liquefied material flows through the holes in the wall and out of the longitudinal opening into structures of the hard tissue and/or hard tissue replacement material. The medical device also comprises a directing structure that is structured angularly with respect to a longitudinal axis of the longitudinal opening to direct different portions of the liquefiable material to different ones of the holes.

'Structured angularly'—or azimuthally—means that the structure is not constant along the circumference but varies as a function of the azimuthal angle. In this, the directing structure is a structure within the cross section of the longitudinal bore, i.e. if, for example, the longitudinal bore has a circular cross section, the directing structure's radial position is at least partly within the radius of the bore.

The holes in the wall of the sheath element (often in the circumferential wall) may be approximately equally distributed around the periphery, or they may be asymmetrically distributed. For example, for certain applications it may be advantageous to have two or three holes at relatively small angular distances of between 30° and 120°, whereas on the other side of the sheath element no holes are present.

The longitudinal bore may be centric or arranged off-center. While for many applications a centric arrangement may be advantageous, for asymmetric implants (such as the shaft of a prosthesis) of for implants from which the outflow is to be asymmetric may be better. Especially, the positioning of the longitudinal bore with respect may influence the dead volume of thermoplastic material remaining in the hole—the thinner the wall at the position of the hole, the less deep the hole, and the smaller the dead volume.

The liquefiable element may be a single, one-piece element. Such a single one-piece element may be advantageous in terms of transmitting mechanical energy from a proximal to a distal end. Alternatively, a plurality of liquefiable elements may be present, such as a plurality of shaped pieces, chips, flakes, etc.

In a medical device according to this principle, the liquefaction takes place by the impinging energy being absorbed in a vicinity of the distal end of the liquefiable element and in a vicinity of the holes. For example, the impinging energy may be mechanical vibration energy, and material of the liquefiable element may be liquefied at an interface between the liquefiable element and the directing structure.

The directing structure is then formed by a stop face, against which the distal end of the liquefiable element is pressed during liquefaction. The distal stop face for the liquefiable element may, for example, close off the longitudinal opening towards the distal side or at least substantially reduce (by for example at least 50%) a distal portion of the longitudinal opening's cross section compared to the proximal portion. An optional, remaining cross section of the longitudinal opening distal portion extending distally from the directing structure may for example serve as a, for example, central (off-center configurations are possible) guiding portion or as a distal hole through which liquefied material portions, depending on the depth and on the diameter of such a distal hole, may be pressed out in addition to the holes in wall of the sheath element.

The directing structure angularly structures the volume proximally of the distal end of the liquefiable element so that different portions of the liquefied material are directed to a determined one of the holes.

It has been found that by this approach, a potential problem encountered with prior art medical devices is solved. If the tissue adjacent to different holes was significantly different in terms of porosity and/or hardness, it could happen that a large part of the liquefied material exited through the one hole where the least resistance for the hydrostatic pressure on the liquefied material is encountered. This could result in an anchoring that is undesiredly anisotropic. Due to the approach according to the first aspect of the invention, there is a more homogeneous distribution of liquefiable material between the holes.

In embodiments of the invention, the directing structure comprises at least one wall protruding proximally from the directing structure body. The wall separates sub-volumes of a distal region of the longitudinal opening where the liquefaction takes place. In this, the wall does not need to have a homogeneous thickness but merely makes an angular separation between different volume sections of the longitudinal opening that each communicate with the different holes, so that portions of the liquefiable material in these volume portions will have a strong tendency or even be forced to exit the longitudinal portions through the particular attributed hole.

In addition to making this angular separation, the wall also serves as energy director where vibration energy tends to be absorbed and where there liquefaction sets in. Due to this, the liquefaction may set in above the holes ('above' here is used to refer to the proximal direction; this does not imply a particular orientation during use) or at least above their distal end, so that a blocking of the holes by remaining solid parts may be reduced or prevented.

In an embodiment, the directing structure further comprises a ramp portion that slopes away from the longitudinal axis towards a distal end of the according hole, so that there is no pronounced edge between the wall and the stop face. The ramp portion may be curved. It may comprise a radius geometry that guides the liquefiable material from an axial to a radial direction within the sheath element.

The wall may protrude further to the proximal direction than holes' most proximal side so that every material that reaches the hole is confined to the volume segment by the wall and is, thus, prevented from getting to an other wall by the hydrostatic pressure acting on the liquefiable material and by its movement. These embodiments are especially suited for cases where a large difference between the resistances encountered for material flowing out of the different holes is to be expected. In other embodiments, the wall protrudes less far the to proximal side than the holes' most proximal portion, but nevertheless the directing effect is there. Preferably, the wall protrudes to at least ¼, at least ⅓ or to at least ½ of the axial extension of the hole or of at least one hole that is adjacent (measured from the most distal side of the holes).

In a first group of embodiments, the directing structure is a structure of the sheath element, i.e. its body is one-piece with the sheath element or rigidly and ex-situ fastened to it.

In a second group of embodiments, the directing structure is a directing structure of an insert element that is insertable in situ. The sheath element's longitudinal bore may then be a through bore reaching from the proximal to the distal end. The sheath element further comprises a stop structure cooperating with the insert element when the latter is inserted from the proximal side to stop the insert element at a desired axial position and to secure it there against more distal movements. The stop structure in general is achieved by the longitudinal bore comprising a non-homogeneous cross section along its longitudinal direction. It may, for example, comprise a shoulder that cooperates with a tapering distal portion of the insert element to form a force fit.

In embodiments of the second group, the longitudinal bore is used as a cannulation that may be used in minimally invasive surgery for guiding the device during insertion.

The device according to the first aspect may be an implant, such as an implant used for anchoring. The implant may be a bone screw and in addition to the anchoring by the liquefiable material comprise a thread. It may alternatively be an implant replacing a bone screw. More in general, the invention relates to any implant that is destined to be anchored in hard tissue and/or hard tissue replacement material.

As an alternative to being an implant, the device according to the first aspect of the invention may be an augmentation device used for augmenting, for example, weak or brittle hard tissue and/or hard tissue replacement material and for thereafter being removed.

Depending on whether the device is an implant or an augmentation device, the walls and/or the holes may be chosen to have appropriate dimensions. Holes with comparably large cross sections are suited for ensuring a strong connection between liquefied and re-solidified material that has flown out of the holes and into structures of the hard tissue and/or hard tissue replacement material. This is useful if the device is to remain implanted, i.e. if it is an implant. Holes with comparably smaller cross sections may be used for augmentation devices—the smaller cross sections at least referring to the circumferential dimension; the axial extension may also then be optionally greater; for example the holes may be elongate slits over more than one thread turns.

Further, the holes may optionally be chosen to be not strictly radial, so that the holes are asymmetric with respect to clockwise vs. anticlockwise rotation of the sleeve element around its longitudinal axis. If the sleeve element having this optional feature also has a thread, this feature may on the one hand be used in an implant to enhance the resistance against an unscrewing twist when the force acting on the liquefied and re-solidified material is not a pure shear force, but has a radial component. It may on the other hand be used in an augmentation device to be removed by favouring separation between liquefiable material within the sheath element and liquefiable material that has flown out of it.

In embodiments, the device may be a pedicle anchor device. The pedicle anchor device is equipped for being used like a pedicle screw, i.e. for being implanted in the vertebra from a dorsal direction (but generally at an angle to the sagittal plane, slightly inward towards the sagittal plane) through the pedicle so that a distal portion of the device protrudes into the vertebral body. A proximal portion of the pedicle anchor device has a head portion that serves for securing an orthopaedic rod or other device that stabilizes the spinal column. The pedicle anchor device, thus, has a head portion and a shaft portion. The shaft portion is capable of being anchored, like a pedicle screw shaft (sometimes referred to as 'stem'), in the vertebra. The head portion may, for example, be formed like head portions of any prior art pedicle screws, or may be formed in accordance with the specifications of a new spine stabilizing system. The main requirement of the head portion is that it serves for either directly being affixed to a rod or other spine stabilizing device or for being affixed to an intermediate device to which a rod (or other spine stabilizing device and/or other intermediate device) can be affixed.

In some embodiments, the pedicle anchor device is a pedicle screw, wherein the shaft is threaded. For example, the thread may have a constant outer diameter (major diameter), whereas a core diameter (minor diameter) is larger at the proximal side than at the distal side. The core diameter may be gradually reduced along the entire length of the threaded section, or the core diameter has a stepped characteristics, or has any other characteristics. In other, alternative embodiments, the core diameter is constant.

In alternative embodiments, the shaft of the pedicle anchor device is not threaded.

In these embodiments, the shaft may have a non-circular cross section. For example, the shaft may be flattish so as to be blade-like. Especially, the shaft may be such as to have, where it penetrates the pedicle, a larger longitudinal than transversal extension such as to follow the pedicle's shape. Such a non-circular cross section may in addition if necessary provide additional stability against twisting movements.

In special embodiments, the shaft may have a non-circular cross section and may be twisted. For example, the shaft may be twisted into about a quarter of a helix so that a blade plane at the distal end is approximately perpendicular to a blade plane at the proximal end of the shaft. For example, a rod receiving portion (or other means for affixing a spinal column stabilizer) may be oriented relative to the twisted shaft so that the blade plane at the proximal end of the shaft is oriented approximately parallel to a longitudinal direction and at the distal end of the shaft is oriented approximately parallel to a transversal direction (these terms of direction are to be understood to apply locally, referring to a spine axis). In embodiments of the second group of embodiments where the shaft does not have a circular cross section but is flattish, the holes from the longitudinal bore outward may especially include openings on each of the two flat sides. Additional holes on at least one of the small sides and/or at the distal end may be present. An additional, axial hole at the distal end may be advantageous during surgery because it allows guidance of the anchor during insertion by means of a K wire or similar device.

Embodiments of devices and methods in accordance with all aspects of the invention may be devices/methods for human surgery, or alternatively for (non-human) animal surgery, especially for surgery of dogs, cats or other pets.

In embodiments, the holes through which the liquefied material flows out during implantation/augmentation, may be on a same axial position, or they may be at different axial positions. The angular positions may be evenly distributed around the circumference. In special embodiments, the angular positions may have a deviating distribution adapted for a particular need. For example, if the implant is destined to be an implant for fusing joint parts, and for being inserted in a joint space, the holes (if more than two) may be concentrated on opposed sides to be in contact with the joint areas.

In special embodiments of any aspect of the invention or of any other anchoring or augmentation process that includes pressing liquefied material out of holes in a sheath element, a multi-tiered anchoring or augmentation may be made, with sequentially anchoring/augmenting in different tiers, to each tier being attributed at least one outflow hole (and preferably a plurality of outflow holes). To this end, after anchoring/augmenting on a first tier, an insert element (which may be a first insert element if the sheath element itself comprises a distal stop face or which may be a second insert element if for the anchoring/augmentation at the first tier already an insert element was used) is inserted from the proximal side and caused to stop at a position immediately underneath the second tier. Then, again a liquefaction process is initiated. This may optionally be repeated for a third, or even a fourth, fifth, etc. tier.

In embodiments where the implant does not have a thread, the outer shape of the implant (and/or of the augmentation device) does not need to be generally circularly cylindrical but may have any contour.

Mechanical vibration or oscillation suitable for devices and methods according to embodiments of the invention that include liquefaction of a polymer by friction heat created through the mechanical vibration has, preferably, a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 µm, preferably around 10 to 30 µm. Rotational or radial oscillation is possible also.

For specific embodiments, a further way for producing the thermal energy for the desired liquefaction comprises coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably, electromagnetic radiation in the visible or infrared frequency range is used, wherein the preferred radiation source is a corresponding laser. Electric heating of one of the device parts may also be possible.

In this text the expression "thermoplastic material being liquefiable e.g. by mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are e.g. produced by ultrasonic devices as e.g. known for dental applications. For being able to constitute a load-bearing connection to the tissue, the material at the time of insertion has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as, for example, polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www.matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, preferentially 10-25% by volume), sub-micron (nanofillers as from precipitation, preferentially plate like aspect ratio>10, 10-50 nm, contents 0.5 to 5% by volume).

A specific example of a material with which experiments were performed was PLDLA 70/30 comprising 30% (weight percent) biphase Ca phosphate that showed a particularly advantageous liquefaction behaviour.

The material of the sheath element (which may be a screw) may be any material that does not melt at the melting temperatures of the liquefiable material. Especially, the sheath element may be of a metal, for example a titanium alloy. A preferred material is titanium grade5. This material, in addition to being generally suited for implantable devices, has a comparably low heat conduction. Because of this bad heat conduction, the melting zone arising in liquefiable material and at the interface to the directing structure is heated quickly, without the surroundings being heated to too high temperatures. Alternative materials for the sheath element are other metals like other titanium alloys, stainless steel, ceramics like Zirconium oxides or Aluminum oxides, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogous elements. The drawings show:

FIGS. 3-5 an embodiment of a sheath element of an implant or augmentation device;

FIG. 6 a detail of a further embodiment of an implant or augmentation device;

FIG. 7 a view of an insert element of the implant or augmentation device of FIG. 6;

DESCRIPTION OF THE PREFERRED EMBODIMENTS

Figure 1A:
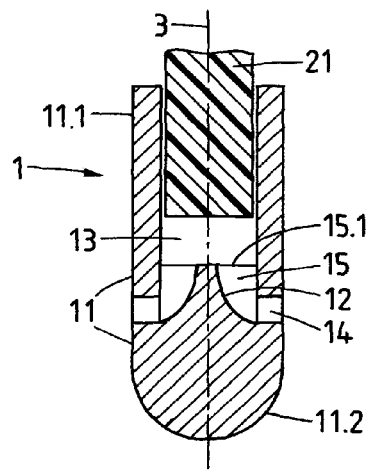
FIGS. 1a and 1b an embodiment of an implant or augmentation device.
Figure 1B:
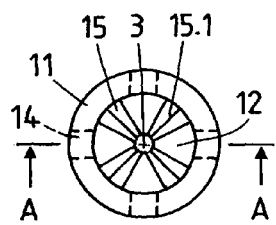

The device schematically depicted in FIGS. 1a and 1b may be a surgical implant, for example for being anchored in hard tissue and/or hard tissue replacement material. It may have a function similar to the function of a surgical screw, and/or of an anchor (such as a suture anchor or an implant to which a dental crown is to be mounted), or it may have a "standalone" function, for example by containing a substance to be delivered to a surrounding tissue, and/or by containing a different device such as an electronic device, etc. Like in all other embodiments of the invention, the device, if being designed to remain in the patient's body after surgical operation, may have any function a surgical device anchored in hard tissue and/or hard tissue replacement material may have in surgery. As an alternative to being designed to remain the patient's body after the surgical operation, the devices according to the different embodiments—unless explicitly stated otherwise—may also be a temporary anchor or may be an augmentation device, for example as taught hereinafter.

The device 1 is insertable into an opening or a gap or the like of hard tissue and/or hard tissue replacement material, essentially by a movement along an implantation axis 3 that is also considered to be a longitudinal axis of the device. The device comprises a sheath element 11 with a proximal wall portion 11.1 that surrounds a longitudinal bore 13 open to the proximal side of the sheath element. A distal end portion 11.2 terminates the longitudinal bore distally. The distal end portion forms the directing structure. The directing structure comprises a ramp portion 12 sloping away in a concave manner from a center around the longitudinal axis. At the radially outer side of the ramp portion, the wall portion of the sheath element has four holes 14 equally distributed around the circumference of the sheath element. At angular positions between the holes, the directing structure further comprises walls 15 angularly sub-dividing a portion of the longitudinal bore volume communicating with the holes 14. In the depicted embodiment, the walls don't have constant thickness and taper towards a proximal edge 15.1.

The device further comprises a liquefiable element 21, namely a polymer pin 21 that is adapted to the sheath element to be inserted in the longitudinal bore 13 from the proximal side.

For the anchoring or augmenting process, the liquefiable element 21 is inserted and brought into a position where it abuts against the directing structure. While the sheath element is in contact with hard tissue and/or hard tissue replacement material 31, the liquefiable element is pressed against the directing structure while energy impinges from the proximal side. Under the additional effect of the pressing force, the liquefied material of the liquefiable element is pressed out through the holes 14 and into structures, like pores, surface unevenness, inhomogeneities etc. of the hard tissue and/or hard tissue replacement material 31.

Figure 1C:
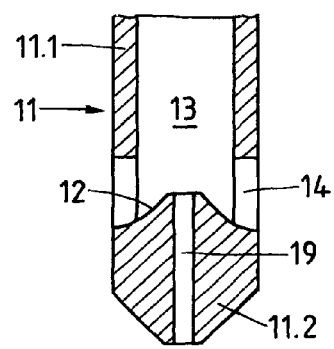
FIGS. 1c and 1d a distal portion of a variant thereof.
Figure 1D:
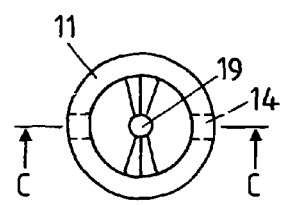

The variant of the sheath element depicted in FIGS. 1c and 1d is distinct from the above-described embodiment by the following features.

a. Instead of four holes 14 along the circumferential wall, only two such holes 14 are present. The directing structure is shaped accordingly. If the directing structure is symmetric, the symmetry of the directing structure is therefore two-fold instead of four-fold as in FIGS. 1a, 1b.

b. The ramp portion 12 of the directing structure is not concave but approximately plane.

c. The holes 14 are not circular or approximately circular but elongate; in the depicted embodiment the axial extension is substantially larger than the extension along the circumferential direction.

d. The directing structure comprises an additional, distal, axial hole 19. A first potential advantage of such a distal hole is guidance. During surgery, a thin element such as a so-called Kirschner wire (K wire) can be directed to the target location, and a distal end may be provisionally fixed there. The sheath element may then be positioned by sliding to the target location on the thin element, whereafter the thin element may be removed. A second potential advantage is an additional distal fixation by liquefiable, liquefied material being pressed out of the distal hole 19, too, and being pressed into structures of the tissue around the exit of the distal hole.

All of these features may be present in combination (as depicted in FIGS. 1c and 1d) or alone (for example, the structure of FIGS. 1a, 1b may be provided with a distal hole 19 with the four holes and the directing structure remaining as they are, etc.). They may also be incorporated in any sub-combination (for example, the structure of FIGS. 1a, 1b may be modified to comprise two holes and a two-fold symmetry, an additional distal hole, but with the concave directing structure and an approximately circular hole shape, etc.

The additional distal hole 19 (if present) may be engineered to serve for pressing out liquefied material or not, depending on the requirements. As a rule, the larger the diameter and the smaller the depth, the more is there a tendency for the liquefied material to be pressed out. Also the amount of sheath element material around the distal hole 19 that participates in cooling the material within the distal hole plays a role. In a sheath element of the kind illustrated in FIG. 1c and made of Titanium, a PLDLA pin has been used as a liquefiable element. In a distal hole 19 of a diameter of 1.7 mm and a length of 3 mm, small amounts of liquefied material have been observed to exit through the distal hole in some experiments, whereas in other experiments the material froze in the hole. The ratio d/l of 1.7/3 may thus be viewed as a threshold in implants of this kind. For larger diameters or shorter depths, there is a reliable effect of material exiting through the distal hole, whereas by smaller diameters or substantially larger depths, the outflow may reliably be prevented due to the material freezing in the hole during the process.

While the particular ratio is characteristic of the shape of FIG. 1c, the same principle applies to other shapes.

A distal hole of the kind shown in FIG. 1c is not necessarily cylindrical. Rather, other shapes may be used, including irregular elements protruding from the wall inwards into the distal hole.

If the distal hole is dimensioned to cause material to flow out, but the surgeon does not want material to flow out distally, a simple plug may be used to close off the distal hole.

Figure 2:
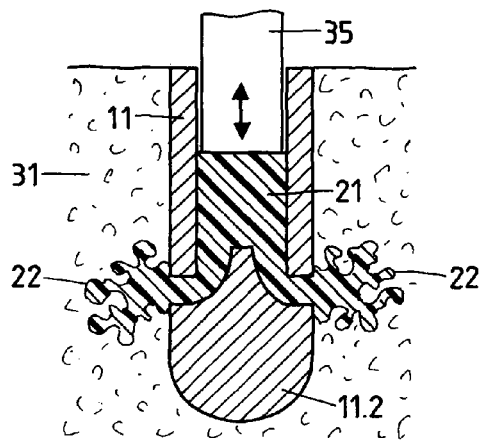
FIG. 2 a cross section through the device of FIGS. 1a and 1b during the implantation or augmentation process.

More in general, a sheath element of embodiments of the invention may comprise any one of or any combination of features a.-d. Instead of feature a., any other number of holes may be present. As illustrated in FIG. 2, an advantageous way of causing energy to impinge is by way of a sonotrode 35 that is pressed against a proximal end face of the liquefiable element while mechanical vibrations are coupled into the sonotrode. The mechanical vibrations are coupled into the liquefiable element 21, and the vibration energy is at least partly absorbed at the interface to the directing structure causing the polymer material of the liquefiable element to at least locally liquefy at this interface. The angular structuring of the directing structure with the walls between the holes firstly has the function to separate portions of the liquefiable element during liquefaction. Due to this, approximately equal amounts of liquefied material is pressed out of every one of the four holes 14, even if the liquefied material while being pressed out of the different holes 14 encounters different resistance. A second function of the walls 15 that protrude distally from the directing structure body and the stop face is that of energy directors. The liquefiable material will have a tendency to start liquefying, under the impact of mechanical vibrations, at edges or other pronounced structures either of the sheath element or of the liquefiable element itself. The energy directing function of the walls 15 is a means for causing the liquefaction to start and take place in vicinity of the holes 14 and not, for example, at the proximal interface to the sonotrode where too early an onset of liquefaction would be undesired.

FIG. 2 illustrates the situation during the anchoring or augmentation process if the sheath element is inserted in a pre-made bore in bone tissue 31. Liquefied and re-solidifying material portions 22 pressed into the surrounding bone tissue 31 and interpenetrating structures of the latter strengthen the tissue that may be cancellous bone or according replacement material. In addition, if the device is an implant meant to remain in the patient's body and portions of the liquefiable material remain, after re-solidifying, in the sheath element, the connection provides a solid anchoring.

FIGS. 3-5 show different views of a further embodiment of a sheath element of a device according to the invention. In addition to the features of the sheath element 11 described referring to FIGS. 1a, 1b, and 2, the sheath element 11 comprises the following features:

e. A collar portion 11.3 that is for example used to fasten a different, not shown element to the hard tissue and/or hard tissue replacement material.

f. The holes 14 have a longer axial (with respect to the longitudinal axis) extension and proximally reach further than the edges 15.1 of the walls 15. The long axial extension is especially suited for devices destined to remain in the patient's body, because they cause a large interface between liquefied material portions interpenetrating the tissue on the one hand and material portions remaining in the sheath element on the other hand.

g. The walls 15 have a portion with a constant thickness ending in the edges 15.1.

h. The ramp portion 12 is not spherical but conical, thus its section with a plane going through the longitudinal axis is a straight line and not concave.

i. The edges 15.1 of the walls 15 slope towards the center.

These features can be realized all in combination (as in the embodiment of FIGS. 3-5) or individually or in any sub-combination, and in any combination with features a.-d., except that features b. and h. both refer to (alternative) ramp portion shapes.

The particular shape of the walls and the ramp portions of the embodiment shown in FIGS. 3-5 features advantages pertaining to the manufacturing of the sheath element. Particularly, it is possible to manufacture the sheath element by adding the longitudinal bore to a pin-shaped blank by drilling and adding, by drilling at an acute angle, the holes 14. In this, the drilling tool may have a conical end portion and may be moved up and down when the holes 14 are made to create their elongate shape. However, the sheath element 11 of FIGS. 3-5, like sheath elements of the other embodiments of this invention, are not restricted to sheath elements made by a particular manufacturing method. Rather, other techniques of manufacturing, including machining techniques and casting techniques, may be used to manufacture the sheath element. The skilled person will know and/or will find an abundance of literature pertaining to the manufacturing of, for example, medical devices of titanium or other metals, ceramics, hard plastics, etc.

FIGS. 6 and 7 show a further embodiment of a medical device. Compared to the previously described embodiments, the embodiment of FIGS. 6 and 7 incorporates the following features:

j. The outer side of the sheath element comprises an outer thread 11.4.

k. The longitudinal bore 13 is a through bore, making the device suitable for being guided by a wire in minimally invasive surgery. The through bore is narrowed towards the distal side so that a shoulder 11.5 is built. The shoulder serves as a stop structure for an insert element 18 that terminates the longitudinal opening for the liquefiable element towards the distal side and that comprises the directing structure including the walls 15 and the ramp portions 12. The insert element comprises a distal tapered portion 19 that together with the shoulder 11.5 co-operates to form a force fit.

Features j. and k. may be realized alone or in combination, and there is the option to combine with any one of features a.-i.

Other stop structures would be possible. For example the sheath element may comprise at least one interior axial groove that reaches from the proximal end of the sheath element to a distal stop and in which a corresponding number of ridges or tongues of the insert element is guided. Such an embodiment features the additional advantage that the angular relative orientation of the sheath element and the insert element is well-defined during insertion. As an even further variant of a stop structure, the insert element may comprise a spring deflected, during insertion in the sheath element, radially inward against a spring force and forcing a stop flange portion into an annular stop groove of the sheath element at the appropriate axial position. Various other stop structures are possible.

Further features of the embodiment of FIGS. 6 and 7 are:

l. The edges 15.1 of the walls 15 slope towards the center (c.f. feature i.)

m. The walls 15 protrude proximally further than the holes 14. By this, the effect of a controlled distribution of liquefied material between the different holes is effective even if the resistance encountered for liquefied material pressed out of the holes differs strongly between the holes because the interface between liquefied material and still solid material may be expected to be proximal of the upper (most proximal) end of the holes 14 (in contrast to feature f.; feature m. may be combined with any other one of features a.-k).

Figure 8:
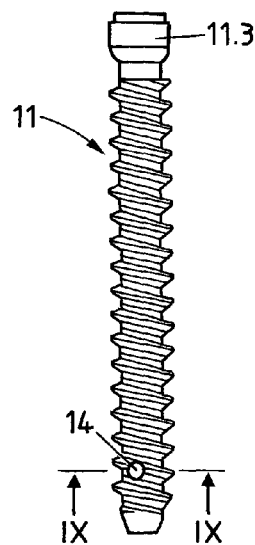
FIGS. 8 and 9 a further embodiment of a sheath element.

FIG. 8 depicts an embodiment of a sheath element 11 of the kind described referring to FIGS. 6 and 7 that is a surgical screw, for example a pedicle screw, or an augmentation device that is suitable for preparing an insertion of a surgical screw, as described hereinafter in more detail.

Figure 9:
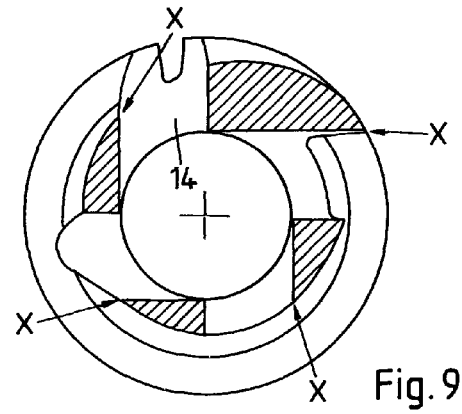

FIG. 9 depicts a section along the plane IX-IX in FIG. 8 illustrating optional features that may be realized in any embodiment, either alone or in combination.

The holes 14 are not strictly radial, but axes of the holes, do not go intersect the proximodistal axis. This brings about an asymmetry of the holes with respect to clockwise vs. anticlockwise rotational movements of the device. This in turn produces sharp edges marked by X in FIG. 9. If the device, after the anchoring or augmentation process, is turned in a direction that corresponds to a clockwise rotation in FIG. 9, the liquefied and re-solidified material remaining in the hole is subject to both, a shearing force and a cutting action by the sharp edges X. This will favor a separation between liquefiable material portions outside of the sheath element and interpenetrating the hard tissue and/or hard tissue replacement material on the one hand and liquefiable material portions remaining in the sheath element on the other hand. A configuration where an unscrewing corresponds to a clockwise rotation in FIG. 9 is thus advantageous in cases where the device is an augmentation device, where the sheath element is to be retracted. If, on the other hand, the device after anchoring is turned in a counter-clockwise direction, the force acting on the liquefied and re-solidified material in the holes 14 will have a radial and an axial component, with reduced shearing forces, and no cutting occurs. In such a situation, there will be a strong resistance to a rotational movement. A configuration where an unscrewing corresponds to a counterclockwise rotation in FIG. 9 is thus advantageous in cases where the device is designed to remain anchored in the body of the patient.

The holes 14 are not at equal axial positions. Rather, the positions may follow the thread. This feature may be advantageous if the sheath element comprises a thread, although an interruption of the thread—if the holes are at equal axial positions or have another axial position distribution—is in most cases not a problem.

The principle of the outflow holes being asymmetrical with respect to a radial direction may be implemented independent of the described aspect of the invention. It may be used for medical devices comprising a sheath element suitable of being brought into contact, during a surgical operation, with live hard tissue and/or with hard tissue replacement material, which is based on the liquefiable material being inserted (pre-assembled or inserted in situ) in a longitudinal bore of the sheath element and where the sheath element comprises at least one hole in the sheath element wall, through which the liquefied material is pressed from the longitudinal bore into the structures (pores or cavities or other structures) of the bone tissue or other hard tissue or hard tissue replacement material in which anchoring is desired.

The hereinbefore described embodiments may, in addition or as an alternative to the mentioned optional features, be provided in the following variants:

Multi-tiered anchoring or augmentation with a plurality of insert elements sequentially inserted, the second, more proximal insert element inserted after anchoring or augmentation with the first, more distal insert element, or with a distal directing structure of the sheath element and with at least one insert element to be placed proximally of the distal directing structure after anchoring with the latter. In this, the sheath element comprises one or more holes for each of the different insert elements or for the distal directing structure and the at least one insert element. The sheath element may comprise a plurality if inner shoulders that have a stepwise reduced cross section towards the distal side, or may comprise different guiding grooves reaching to different distal positions for the different insert elements.

The number of holes 14 attributed to a particular directing structure does not need to be four as in the illustrated embodiments but may be two (like in FIGS. 1c and 1d), three, five, six, etc. Also, the angular (azimuthal) spacing does not need to be equal between all holes but may be adapted to a particular situation. For example, for introduction of an implant in a gap of a joint, the sheath element may comprise two pairs of neighboring, relatively close holes at opposite sides. In the case of multi-tiered anchoring, each tear may have an individual number and distribution of holes.

The holes may have different shapes and/or different sizes.

The multi-tiered anchoring or augmentation as described herein thus comprises a first liquefaction process taking place with a first directing structure,—of the sheath element or of an initially separate insert element—the subsequent (after an at least partial re-solidification of the liquefied material) addition of a further directing structure of a (second) insert element and then a second liquefaction. This multi-tiered anchoring or augmentation may be applied independent of the aspect of the invention, i.e. also in situations where a directing structure against which the liquefiable material is pressed is not angularly structured.

Figure 10:
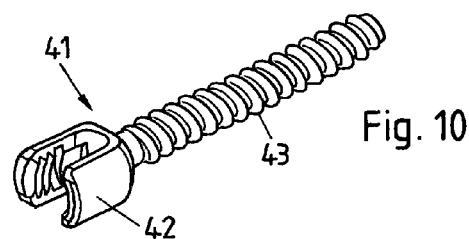
FIGS. 10-12 a pedicle screw being an even further embodiment of a sheath element and being an embodiment of a pedicle anchor device.
Figure 11:
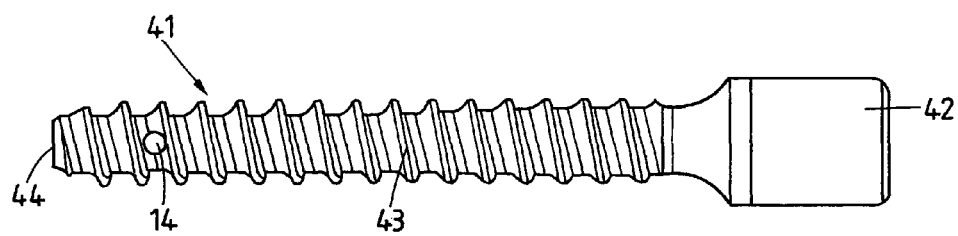
Figure 12:
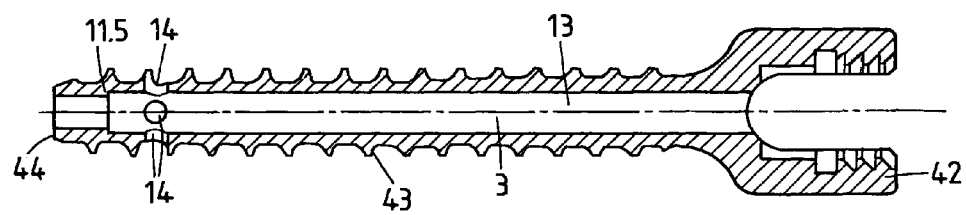

Referring to FIGS. 10, 11, and 12, a bone screw, namely a pedicle screw 41 based on the first aspect of the invention is depicted.

The pedicle screw 41 comprises a screw head 42, a threaded section 43, and a distal end portion 44. The pedicle screw further comprises a longitudinal through bore 13 that, towards the distal end, comprises a narrowed portion so that a shoulder 11.5 for stopping the insert element (not shown in FIGS. 10-12, the type thereof may for example be similar to the one of the device of FIG. 7) inserted from the proximal side is formed.

The thread has a constant outer diameter (major diameter), whereas a core diameter (minor diameter) is larger at the proximal side than at the distal side. More concretely, in the depicted embodiment, in a central portion of the threaded section the core diameter gradually reduces, whereas in peripheral portions the core diameter is constant. In other, alternative embodiments, the core diameter is constant, is gradually reduced along the entire length of the threaded section, or the core diameter has stepped characteristics as taught in WO 90/02526, or has any other characteristics. Also, the outer diameter of the threaded section need not be constant. Generally, the approach according to aspects of the invention may be combined with any suitable outer thread. Compared to prior art pedicle screws with a longitudinal bore, the bore diameter is comparably large to make insertion of the liquefiable element—that may be a polymer pin—possible. In the depicted embodiment, the bore diameter at the more proximal portion of the threaded section is 3.1 mm and at the distal portion of the threaded section is 2.9 mm, whereas the major diameter is 6.6 mm and the minor diameter is between 4.4 mm and 5.3 mm. The resulting wall strength has proven to be sufficient.

The screw head is flattened and comprises an inner thread that can be used for coupling to an apparatus for automated insertion, as described hereinafter.

The invention claimed is:

1. A medical device, comprising:
a sheath element suitable of being brought into contact, during a surgical operation, with live hard tissue and/or with hard tissue replacement material, the sheath element having a longitudinal bore defining a longitudinal opening reaching from a proximal end of the sheath element into a distal direction, and a plurality of holes in a wall of the opening,
a liquefiable element that is insertable or inserted in the longitudinal opening and at least partly liquefiable by the impact of energy impinging from a proximal side so that liquefied material flows through the holes in the wall and out of the longitudinal opening into structures of the hard tissue and/or hard tissue replacement material, and
a directing structure comprising walls that extend radially toward an inner surface of the sheath element and serve to direct different portions of the liquefiable material to different ones of the holes.

2. The medical device according to claim 1, wherein the directing structure includes a directing structure body terminating the longitudinal opening distally, and wherein the walls protrude proximally from the directing structure body.

3. The medical device according to claim 2, wherein each of the walls extends between two of the holes toward a center of the longitudinal opening.

4. The medical device according to claim 2, wherein the walls comprise a proximal edge capable of cutting into the liquefiable element while the energy impinges.

5. The medical device according to claim 1, wherein the directing structure is a directing structure of the sheath element.

6. The medical device according to claim 1, wherein the longitudinal bore is a through bore and the inner surface of the sheath element comprises a stop structure; and wherein the device further comprises an insert element insertable in the bore, said insert element comprising the directing structure, the insert element being shaped to rest against the stop structure when inserted into the longitudinal bore from the proximal side thereof.

7. The medical device according to claim 6, wherein the stop structure cooperates with the insert element to define a force fit.

8. The medical device according to claim 1, wherein the directing structure comprises at least one ramp portion sloping away from the longitudinal axis towards a distal end of one of the holes.

9. The medical device according to claim 1, wherein the sheath element further comprises an outer thread.

10. The medical device according to claim 1, wherein the device is an implant.

11. The medical device according to claim 1, wherein the device is an augmentation device equipped for reinforcing hard tissue and/or hard tissue replacement material by the liquefiable material interpenetrating structures of the hard tissue and/or hard tissue replacement material.

12. The device according to claim 1, wherein the device is a pedicle anchor device for being implanted in a human or animal vertebra from a generally dorsal direction through one of the pedicles of the vertebra so that a distal portion of the anchor device protrudes into the vertebral body of the vertebra, the pedicle anchor device comprising a proximal head portion for securing an orthopaedic device for stabilizing the spinal column, and comprising a distal shaft portion capable of being anchored in the vertebra, the longitudinal opening reaching from the proximal head portion into the shaft portion.

13. The device according to claim 12, wherein the shaft portion comprises an outer thread.

14. A method of anchoring a device in a human or animal body, the method comprising the steps of:
 providing a sheath element with a longitudinal bore defining a longitudinal opening reaching from a proximal end of the sheath element into a distal direction, and a plurality of holes in a wall of the opening,
 providing a liquefiable material,
 bringing the sheath element into contact with hard tissue of the human or animal body and/or hard tissue replacement material,
 pressing the liquefiable material towards a distal direction and against a directing structure comprising walls that extend radially toward an inner surface of the sheath element while it is at least partially in the longitudinal bore and simultaneously impinging the liquefiable material with mechanical vibrations to cause the liquefiable material to be at least partially liquefied and to be pressed out through the holes and into the hard tissue and/or hard tissue replacement material, wherein the directing structure separates portions of the liquefiable material pressed out through different ones of the holes; and
 causing the liquefiable material to re-solidify to provide an anchor for the sheath element in the hard tissue and/or hard tissue replacement material.

\* \* \* \* \*